United States Patent
Thomas et al.

(10) Patent No.: US 11,246,980 B2
(45) Date of Patent: Feb. 15, 2022

(54) PUMP DEVICE HAVING A HOLDING DEVICE FOR RECEIVING A SYRINGE

(71) Applicant: Fresenius Vial SAS, Brézins (FR)

(72) Inventors: Fabien Thomas, Saint Victor de Cessieu (FR); Rémy Wolff, Morette (FR); Nicolas Charles, Chirens (FR); Denis Bertagnolio, Sillans (FR)

(73) Assignee: Fresenius Vial SAS, Brézins (FR)

( * ) Notice: Subject to any disclaimer, the term of this patent is extended or adjusted under 35 U.S.C. 154(b) by 218 days.

(21) Appl. No.: 16/629,561

(22) PCT Filed: May 29, 2018

(86) PCT No.: PCT/EP2018/064070
§ 371 (c)(1),
(2) Date: Jan. 8, 2020

(87) PCT Pub. No.: WO2019/011518
PCT Pub. Date: Jan. 17, 2019

(65) Prior Publication Data
US 2021/0154393 A1    May 27, 2021

(30) Foreign Application Priority Data
Jul. 12, 2017   (EP) .................................. 17305916

(51) Int. Cl.
*A61M 5/145*    (2006.01)
(52) U.S. Cl.
CPC ........ *A61M 5/1456* (2013.01); *A61M 5/1454* (2013.01); *A61M 5/1458* (2013.01)
(58) Field of Classification Search
CPC . A61M 5/1456; A61M 5/1458; A61M 5/1454
See application file for complete search history.

(56) References Cited

U.S. PATENT DOCUMENTS

| 7,153,290 B2 | 12/2006 | Wakabayashi et al. |
| 2010/0063447 A1 | 3/2010 | Stempfle et al. |

(Continued)

FOREIGN PATENT DOCUMENTS

| CN | 102639176 | 8/2012 |
| CN | 105025958 | 11/2015 |

(Continued)

OTHER PUBLICATIONS

International Search Report and Written Opinion, counterpart International Appl. No. PCT/EP2018/064070 (dated Aug. 1, 2018) (11 pages).

(Continued)

*Primary Examiner* — Brandy S Lee
(74) *Attorney, Agent, or Firm* — Cook Alex Ltd.

(57) ABSTRACT

A pump device (1) for administering a medical fluid to a patient comprises a holding device (10) for receiving a syringe barrel (20) of a syringe (2), the holding device (10) comprising a stationary section (101) and a holding member (11) movable with respect to the stationary section (101) between an opened position and a closed position, wherein the holding member (11) is configured to secure, in the closed position, the syringe barrel (20) of a syringe (2) received on the holding device (10) with respect to the stationary section (101). A shaft (130) is coupled to the holding member (11), the shaft (130) being constituted to rotate during a movement of the holding member (11). Herein, a damping device (14) comprises a movable part (140) connected to the shaft (130) and rotatable together with the shaft (130) and a stationary part (141) fixed with respect to the stationary section (101) of the holding device (10), a rotational movement of the movable part (140) with respect to the stationary part (141) providing for a damping of the movement of the holding member (11). In this way a (Continued)

pump device for administering a medical fluid to a patient is provided which may provide for a secure fastening of a syringe barrel and at the same time helps to avoid a damaging of in particular smaller syringes by clamping forces of the holding member.

11 Claims, 7 Drawing Sheets

(56) References Cited

U.S. PATENT DOCUMENTS

| | | |
|---|---|---|
| 2010/0065700 A1 | 3/2010 | Traversaz et al. |
| 2012/0216805 A1 | 8/2012 | Brunnberg et al. |
| 2016/0001004 A1 | 1/2016 | Fourt et al. |

FOREIGN PATENT DOCUMENTS

| | | | |
|---|---|---|---|
| CN | 106725719 | | 5/2017 |
| EP | 1362606 | A1 | 11/2003 |
| EP | 2345441 | A1 | 7/2011 |
| EP | 2910264 | A1 | 8/2015 |
| FR | 2911662 | A1 | 7/2008 |
| GB | 19812 | | 4/1907 |
| GB | 2434738 | A | 8/2007 |
| WO | WO2005/102416 | A1 | 11/2005 |
| WO | WO2015/062926 | A1 | 5/2015 |
| WO | WO-2015062926 | A1 * | 5/2015 .......... A61M 5/1452 |

OTHER PUBLICATIONS

Search Report, counterpart Chinese App. No. 201880041981.0 (dated Jun. 27, 2021) (1 page).
Office Action, counterpart Chinese App. No. 201880041981.0 (dated Jul. 2, 2021) (11 pages) (with English translation).

* cited by examiner

PUMP DEVICE HAVING A HOLDING DEVICE FOR RECEIVING A SYRINGE

The present application is a U.S. National Stage of PCT International Patent Application No. PCT/EP2018/064070, filed May 29, 2018, which claims priority to EP Application No. 17305916, filed Jul. 12, 2017, both of which are hereby incorporated herein by reference.

The invention relates to a pump device for administering a medical fluid to a patient according to the preamble of claim 1.

A pump device of this kind comprises a holding device for receiving a syringe barrel of a syringe, the holding device comprising a stationary section and a holding member movable with respect to the stationary section between an opened position and a closed position. Herein, the holding member is configured to secure, in the closed position, the syringe barrel of a syringe received on the holding device with respect to the stationary section. The pump device furthermore comprises a shaft coupled to the holding member, the shaft being constituted to rotate during a movement of the holding member.

The holding device hence functions as a receptacle for receiving a syringe barrel of a syringe. By means of the holding member the syringe barrel is secured on the stationary section of the holding device such that the syringe barrel is held on the pump device. Hence, upon completion of the installation of a syringe, a piston of the syringe can be pushed into the syringe barrel in order to deliver a medical fluid from the syringe barrel towards a patient.

On the one hand a holding device of this kind must provide for a reliable arrangement of a syringe on the pump device. The EN 60601-2-24 Ed. 3 standard in this regard defines that the syringe barrel must be held in place onto the pump device even if a tearing force of at least 15 N for at least 15 s is applied onto the barrel, hence requiring a sufficient clamping force of the holding member to securely fasten the syringe barrel on the holding device. Nevertheless, during operation of the pump device, the clamping forces acting onto the syringe must not cause a crack in the barrel skin that would let air enter into the syringe barrel causing a so-called free flow condition during which fluid may in a free and uncontrolled manner flow by gravity out of the syringe barrel towards the patient.

For this reason, WO 2015/062926 A1 suggests to use a damping device for damping a rotational movement of the holding member. Herein, in the solution of WO 2015/062926 A1 a rotation of the holding member causes a translation of a shaft, which is damped by a damping device comprising a toothed element.

A pump device comprising a holding device having a rotatable holding member is for example disclosed in U.S. Pat. No. 7,153,290.

It is an object of the instant invention to provide a pump device for administering a medical fluid to a patient which may provide for a secure fastening of a syringe barrel and at the same time helps to avoid a damaging of in particular smaller syringes by clamping forces of the holding member.

This object is achieved by means of a pump device comprising the features of claim 1.

Accordingly, the pump device comprises a damping device comprising a movable part connected to the shaft and rotatable together with the shaft and a stationary part fixed with respect to the stationary section of the holding device, a rotational movement of the movable part with respect to the stationary part providing for a damping of the movement of the holding member.

The damping device hence comprises a movable part and a stationary part. The movable part is connected to the shaft and, when moving the holding member of the holding device, is rotated together with the shaft. A rotation of the shaft hence is transferred to the movable part of the damping device, causing the movable part of the damping device to rotate with respect to the stationary part of the damping device. The damping device provides for a damping of the movement of the movable part relative to the stationary part, by which also the movement of the holding member with respect to the stationary member of the holding device is dampened.

The shaft, in one embodiment, is fixedly connected to the holding member. The shaft herein defines an axis of rotation about which the holding member is rotatable, the holding member hence rotating together with the shaft.

In an alternative embodiment it however is also conceivable that the holding member is movable with respect to the stationary section in a translational fashion. In this case the holding member may be coupled to the shaft for example by a suitable gearing translating the movement of the holding member into a rotation of the shaft.

In one embodiment, the movable part of the damping device is arranged on the shaft and is fixedly connected to the shaft. The movable part hence rotates together with the shaft when the holding member is moved. The movable part herein is coaxial to the shaft and rotates together with the shaft around a common axis of rotation.

In one embodiment, the pump device comprises a drive device comprising a spring element arranged on the shaft for biasing the holding member towards the closed position. By means of the drive device a torque is exerted on the holding member such that the holding member applies a clamping force onto a syringe barrel received on the stationary section. By means of the spring element, hence, a spring elastic force is provided by means of which the syringe barrel of the syringe is held on the holding device.

The spring element may, in one embodiment, have the shape of a coil spring extending about the shaft. The spring element hence is wrapped around the shaft and, when moving the holding member towards the opened position, is (further) tensioned such that the holding member is driven back towards the closed position upon releasing the holding member.

The spring element may have a rather high spring constant (e.g. using a spring of rather high stiffness) such that the holding member may exert a rather high clamping force on the syringe barrel of the syringe to securely fix the barrel to the pump device. In particular, the spring element properties may be chosen in such a way that the EN 60601-2-24 Ed. 3 standard is met. For example, the spring element is configured in such a way that a tearing force of at least 15 N applied for at least 15 s onto the syringe barrel thanks to the connection line does not cause a release of the syringe.

Even if the spring element has a high spring constant such that the holding member will exert a rather high clamping force on the syringe barrel in the closed position, the damping device prevents damage to the syringe (in particular to the barrel of a smaller syringe) because it slows down the rotation of the holding member during the closing movement in that it absorbs part of the kinetic energy of the holding member to reduce the impact strength on the syringe barrel.

For installing a syringe on the pump device, the holding member is for example manually moved from the closed position to the opened position such that the syringe barrel of the syringe can be placed on the stationary section of the holding device. Upon releasing the holding member, the holding member due to the biasing force of the spring element automatically moves back towards the closed position and in this way exerts a clamping force on to the syringe barrel such that the syringe barrel is securely fastened on the stationary section.

The stationary section may for example comprise a concave face for receiving the syringe barrel. Likewise, the holding member may have a concave face for beneficially abutting the syringe barrel.

In one embodiment, the stationary part of the damping device encloses a chamber in which the movable part is rotatable. The chamber may for example (at least partially) be filled with a damping fluid such that by rotating the movable part within the chamber defined by the stationary part it is acted onto the damping fluid which in this way is caused to flow past the movable part and in this way dampens the movement of the movable part with respect to the stationary part.

The damping fluid may in particular be a viscous fluid, in particular a liquid such as grease.

The stationary part of the damping device may, in one embodiment, have a cylindrical barrel shape defining a cylindrical chamber in which the movable part is rotatable. The cylinder axis herein beneficially is aligned with the rotational axis defined by the shaft.

In one embodiment, the stationary part is held in a positive locking manner on a fixing section of the holding device. The fixing section may for example have a face by which the fixing section surrounds the barrel-shaped stationary part such that the fixing section provides for a connection of the stationary part of the damping device to the stationary section of the holding device.

Herein, the stationary part may for example comprise a protrusion element radially protruding from a cylindrical circumference of the stationary part and abutting a stop face, for example in the shape of an edge, a web or a groove, of the fixing section. By means of the protrusion element abutting the stop face, hence, the stationary part is held rotationally fixed with respect to the fixing section such that the stationary part of the damping device is held in position with respect to the stationary section of the holding device during movement of the holding member.

The pump device constitutes a syringe pump for administering a medical fluid from the syringe barrel of a syringe towards a patient. Herein, the pump device in one embodiment comprises a pusher device for acting onto a piston of the syringe to push the piston into the syringe barrel in order to deliver fluid from the syringe barrel towards the patient.

The idea underlying the invention shall subsequently be described in more detail with respect to the embodiments shown in the figures. Herein, FIG. 1 shows a view of a pump device in the shape of a syringe pump;

Figure 2:
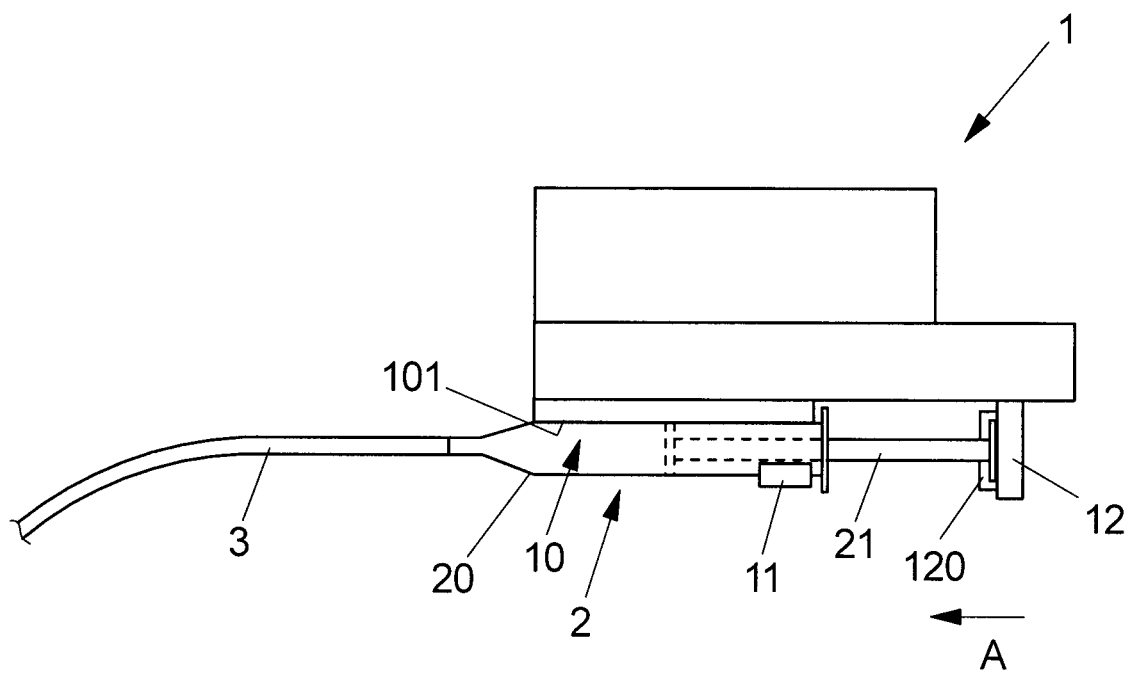
FIG. 2 shows a schematic view of the pump device.
Figure 3:
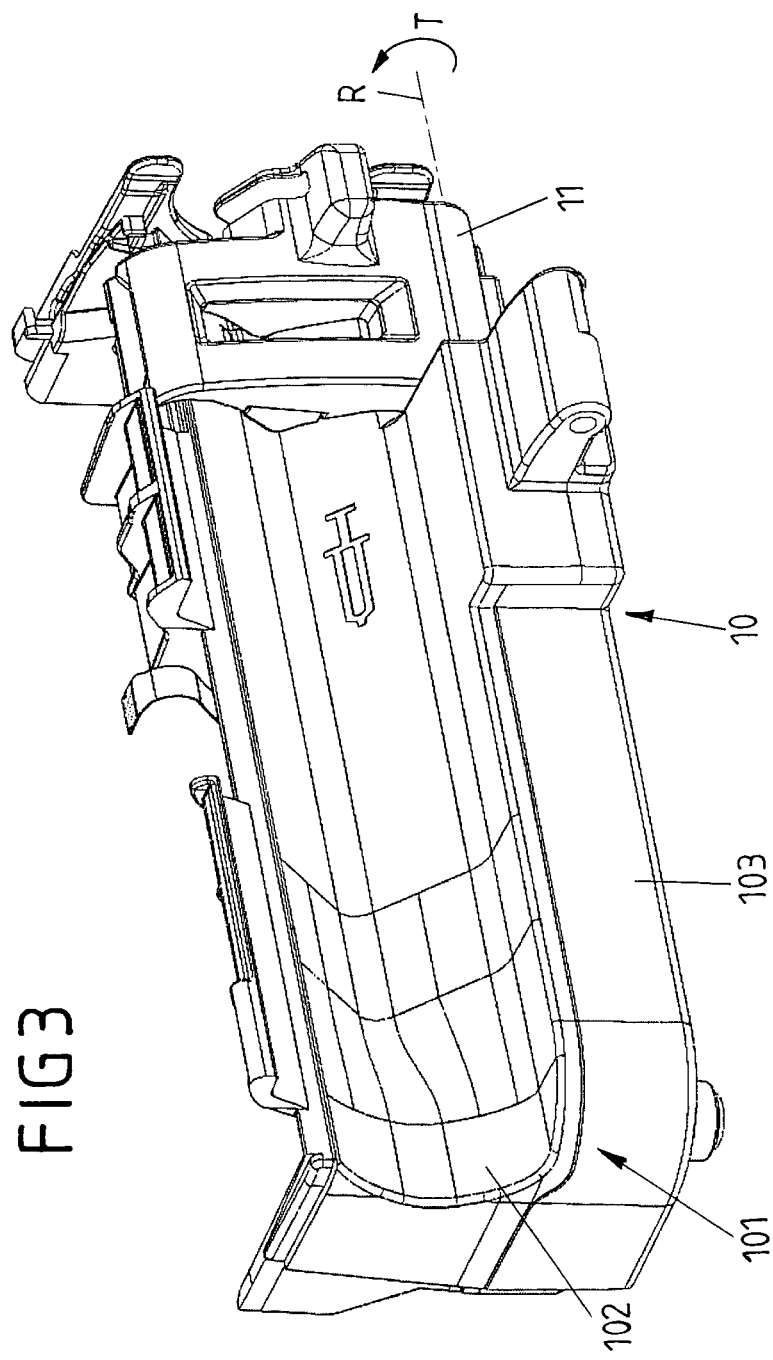
FIG. 3 shows a view of a holding device of the pump device.
Figure 4:
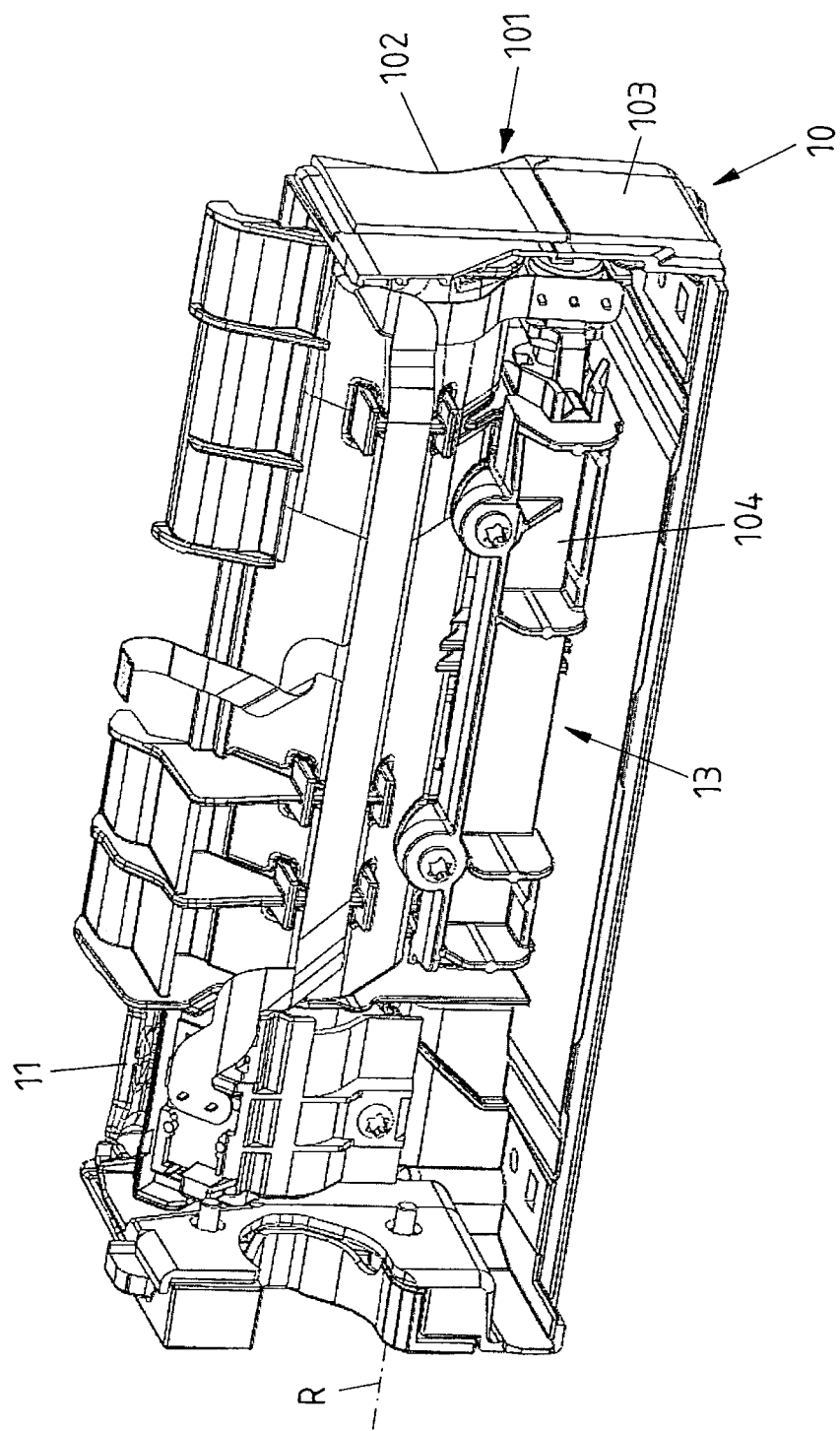
FIG. 4 shows a back view of the holding device.
Figure 5:
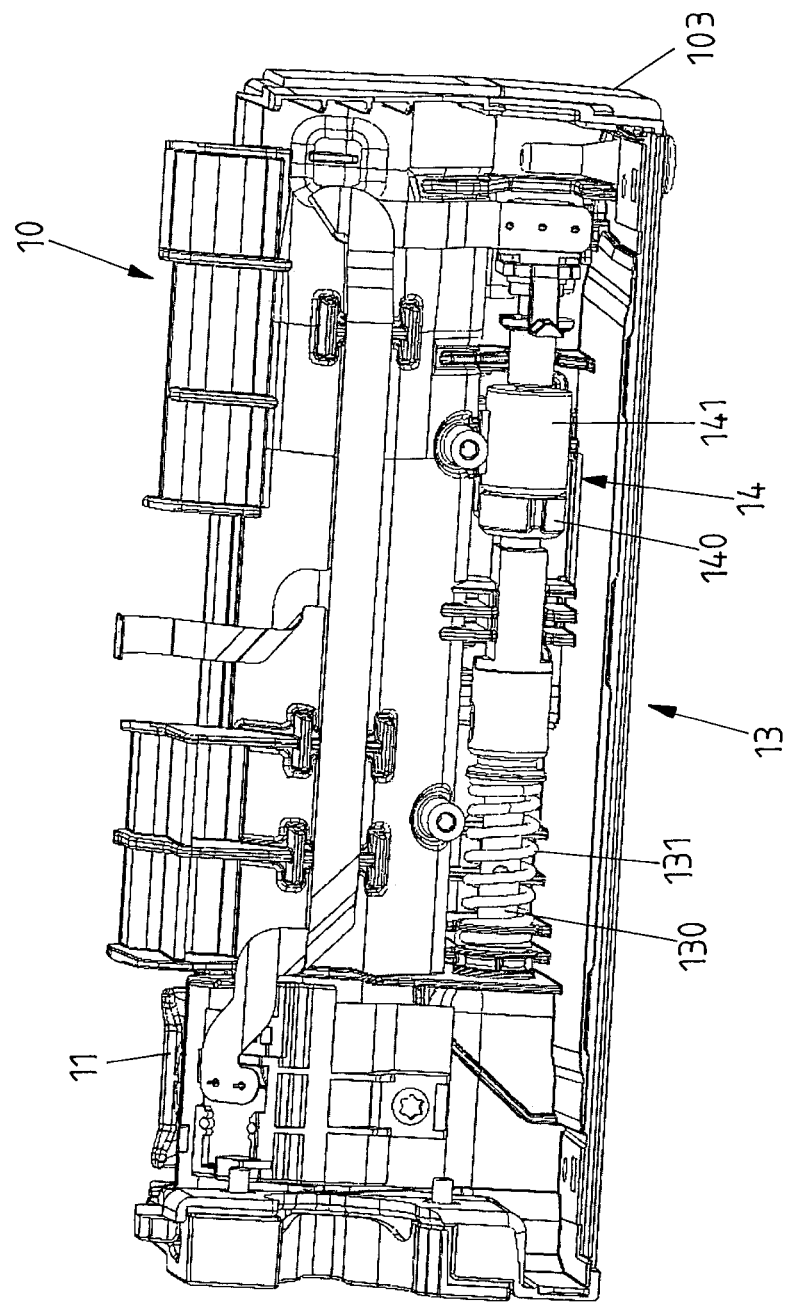
FIG. 5 shows a view of the holding device comprising a drive device for biasing the holding member towards a closed position.

As schematically shown in FIG. 2, upon installation a syringe 2 is placed on a stationary section 101 of the holding device 10 and is held on the stationary section 101 by means of a holding member 11 clampingly fixing a syringe barrel 20 of the syringe 2 on the stationary section 101.

When the syringe 2 is installed on the pump device 1, a piston 21 movable within the syringe barrel 20 of the syringe 2 is coupled to a pusher device 12 of the pump device 1, such that by moving the pusher device 12 in an actuation direction A the piston 21 is pushed into the syringe barrel 20 and a fluid contained in the syringe barrel 20 is delivered through a connection line 3 towards a patient. The piston 21 herein is held on the pusher device 12 by means of a gripper 120 providing for a close connection between the piston 21 and the pusher device 12, allowing also for example to move the piston device 21 out of the syringe barrel 20 in a direction opposite to the actuation direction A.

Figure 1:
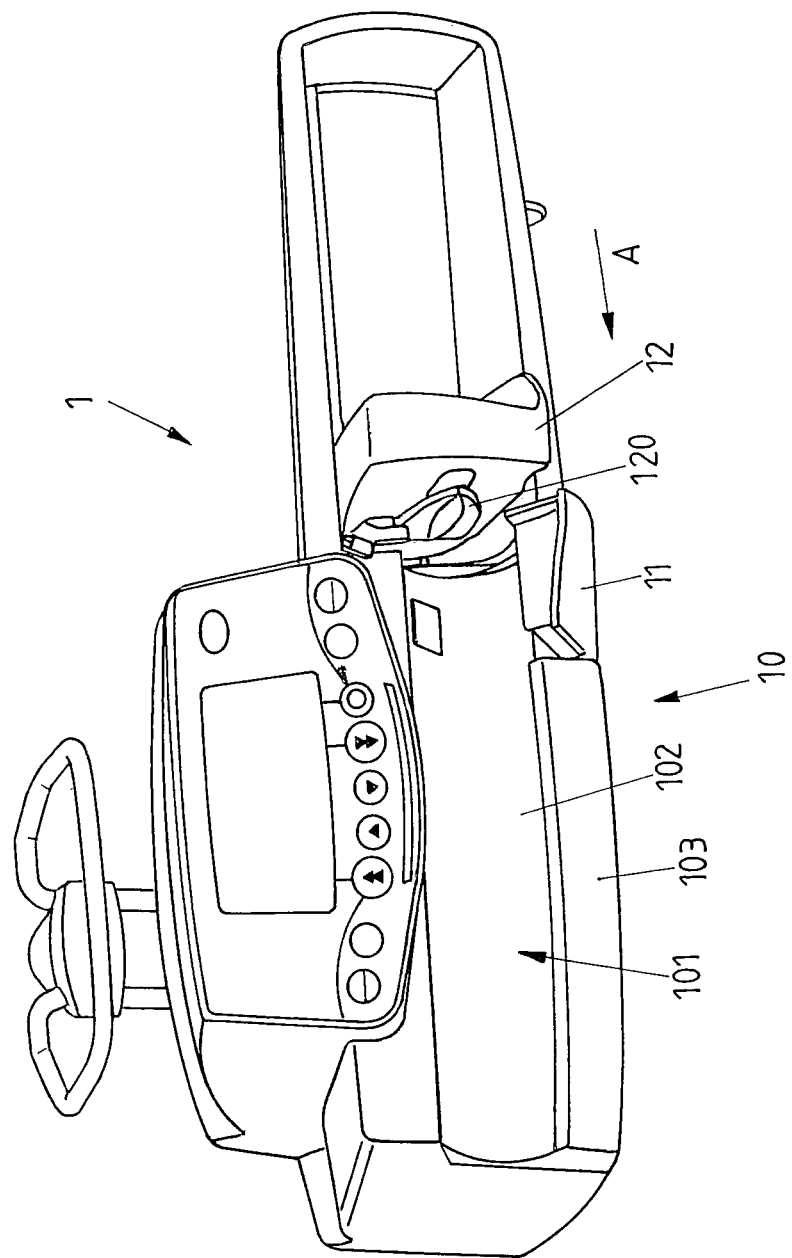
FIG. 1 shows a view of a pump device 1 in the shape of a syringe pump comprising a holding device 10 for receiving a syringe.

As visible from FIG. 1, the stationary section 101 of the holding device 10 comprises a concave face 102 in which the syringe barrel 20 of the syringe 2 can be placed. The concave face 102 is formed in a housing section 103 with respect to which the holding member 11 is rotatable.

In particular, the holding member 11 can be rotated between a closed position and an opened position. In the opened position (see FIG. 1) the holding member 11 allows for placing a syringe barrel 20 of a syringe 2 on the stationary section 101. By closing the closing member 11 a clamping force is exerted on the syringe barrel 20 such that the syringe barrel 20 is held in place on the stationary section 101 by means of the holding member 11.

A specific embodiment of a holding device 10 of a pump device 1 is shown in FIGS. 3 to 6. In this embodiment, the holding member 11 is biased towards the closed position (see FIG. 3) by means of a drive device 13 comprising a shaft 130 defining an axis of rotation R. The holding member 11 is fixedly connected to the shaft 130 such that the shaft 130 is rotated about the rotational axis R when moving the holding member 11 between its closed position and its opened position.

The shaft 130 is for example mounted in a rotatable fashion with respect to the stationary section 101, for example by means of suitable bearings.

The holding member 11, in the shown embodiment, is biased towards the closed position by means of a spring element 131 in the shape of a coil spring extending about the shaft 130. The spring element 131 exerts a biasing force on the shaft 130 and, via the shaft 130, on the holding member 11 such that the holding member 11 abuts a syringe barrel 20 of a syringe 2 placed on the holding device 10 in a clamping fashion.

The spring element 131 may for example be a compression spring exerting a compressional force to bias the holding member 11 towards the closed position, as it is described for example in EP 2 910 264 A1, whose contents shall be incorporated by reference herein.

For actuation, a user for example manually may grab the holding member 11 and may move it from its closed position towards its opened position to place a syringe 2 on the holding device 10. Upon installation of the syringe 2 on the pump device 1 the user may release the holding member 11 such that the holding member 11, due to the biasing force of the spring element 131, moves back into its closed position.

To herein prevent that the holding member 11 snaps back towards the closed position—which may otherwise damage a syringe barrel 20 of a syringe 2 received on the stationary section 101, in particular for a smaller syringe 2—a damping device 14 is provided to dampen a rotational movement of the shaft 130.

The damping device 14 has the shape of a cylindrical barrel and is arranged coaxially to the rotational axis R defined by the shaft 130. The damping device 14 comprises a movable part 140 which is fixedly connected to the shaft 130 and, upon rotation of the shaft 130, is rotated together with the shaft 130. The movable part 140 is received within a stationary part 141 having a generally cylindrical shape, a movement of the movable part 140 with respect to the stationary part 141 being damped such that, in this way, a movement of the holding member 11 towards the closed position is braked.

Figure 6:
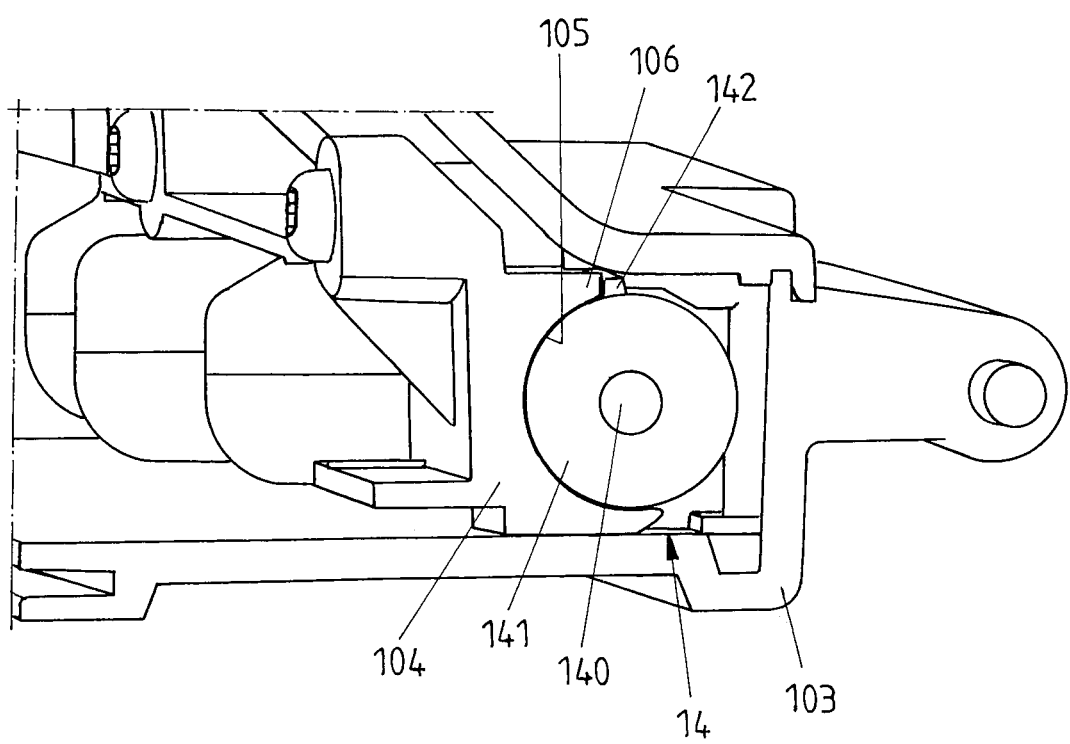
FIG. 6 shows a view of a damping device on a stationary section of the holding device.

The stationary part 141 is in abutment with a fixing section 104 fixedly connected to the housing section 103 forming the stationary section 101 of the holding device 10, as can be seen from FIG. 6. The fixing section 104 herein defines a concave inner face 105 which is in abutment with the cylindrical, circumferential outer face of the stationary part 141 such that a radially protruding element 142 of the stationary part 141 rests against a stop face 106 of the fixing section 104. In this way the stationary part 141 is fixed with respect to the housing section 103 in a torque-proof manner such that, when moving the holding member 11, the stationary part 141 remains in position with respect to the housing section 103 and the stationary section 101.

Figure 7:
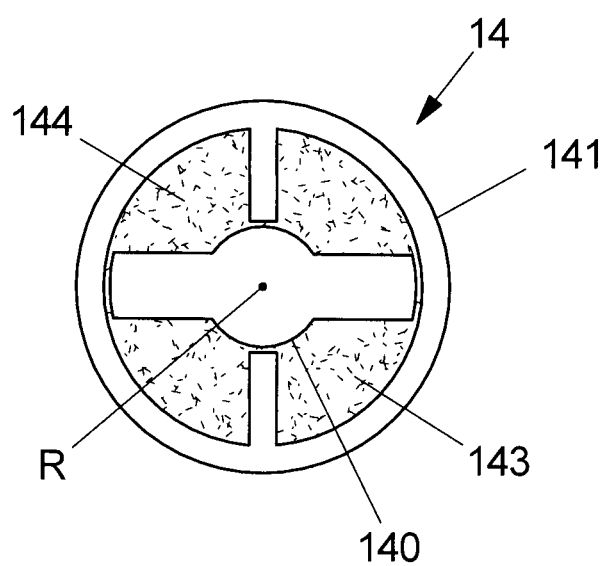
FIG. 7 shows a schematic cross-sectional view of the damping device.

In one embodiment, as schematically shown in FIG. 7, the stationary part 141 defines a chamber 143 which (at least partially) is filled with a damping fluid 144, for example a grease liquid. Within the chamber 143 the movable part 140 is rotatable about the axis of rotation R such that, when rotated, the movable part 140 acts onto the damping fluid 144 and causes the damping fluid 144 to flow past radial wings of the movable part 140.

In this way kinetic energy is taken up such that a damping action is provided which slows down the rotational movement of the movable part 140 within the stationary part 141 and in this way dampens the movement of the holding member 11.

Because the rotation of the shaft 130 is directly translated into a rotation of the movable part 140, a rotation of the holding member 11 by for example 90° causes a rotation of the movable part 140 within the chamber 143 of the stationary part 141 by 90°. This may provide for an efficient damping of the movement of the holding member 11, at an easy and cost-efficient construction of the damping device 14.

The idea of the invention is not limited to the embodiments described above, but may be implemented in an entirely different fashion.

In particular, the pump device may have a different constitution and structural built. The pump device may be suitable to receive syringes of different sizes and different manufacturers, wherein due to the damping of the movement of the holding member the risk for damaging the syringes upon installation on the pump device is largely reduced.

Also, the damping device may have an entirely different shape and structure and may work according to a different functional principle than described herein.

The holding member may be movable in a translational fashion (instead of being rotatable) and in this case may be coupled to the shaft via a suitable gearing.

LIST OF REFERENCE NUMERALS

1 Pump device
10 Holding device
101 Stationary section
102 Concave face
103 Housing section
104 Fixing section
105 Face
106 Stop face
11 Holding member
12 Pusher device
120 Gripper
13 Drive device
130 Shaft
131 Spring element
14 Damping device
140 Movable part
141 Stationary part
142 Protrusion element
143 Chamber
144 Damping fluid (grease)
2 syringe
20 Cylindrical tube
21 Piston
3 Line
A Actuation direction
R Axis of rotation
T Tensioning direction

The invention claimed is:

1. A pump device for administering a medical fluid to a patient, the pump device comprising:
   a holding device for receiving a syringe barrel of a syringe, the holding device comprising a stationary section and a holding member movable with respect to the stationary section between an opened position and a closed position, wherein the holding member is configured to secure, in the closed position, the syringe barrel of a syringe received on the holding device with respect to the stationary section,
   a shaft coupled to the holding member, the shaft being configured to rotate during a movement of the holding member, and
   a damping device comprising a movable part connected to the shaft and rotatable together with the shaft and a stationary part fixed with respect to the stationary section of the holding device, a rotational movement of the movable part with respect to the stationary part providing for a damping of the movement of the holding member.

2. The pump device according to claim 1, wherein the shaft is fixedly connected to the holding member.

3. The pump device according to claim 1, wherein the shaft defines an axis of rotation about which the holding member is rotatable together with the shaft.

4. The pump device according to claim 1, wherein the movable part is fixedly connected to the shaft and rotatable together with the shaft about a common axis of rotation.

5. The pump device according to claim 1, further comprising a drive device comprising a spring element arranged on the shaft for biasing the holding member towards the closed position.

6. The pump device according to claim 5, wherein the spring element is a coil spring extending about the shaft.

7. The pump device according to claim 1, wherein the stationary part of the damping device encloses a chamber in which the movable part is rotatable.

8. The pump device according to claim 7, wherein the stationary part has a cylindrical barrel shape.

9. The pump device according to claim 7, wherein the chamber comprises a damping fluid.

10. The pump device according to claim 1, wherein the stationary part is held, in a positive locking manner, on a fixing section connected to the stationary section of the holding device.

11. The pump device according to claim 10, wherein the stationary part of the damping device comprises a protrusion element abutting a stop face of the fixing section.

* * * * *